US006306662B1

(12) United States Patent
Menzel (10) Patent No.: US 6,306,662 B1
(45) Date of Patent: Oct. 23, 2001

(54) FINGERPRINT DEVELOPMENT METHODS

(75) Inventor: E. Roland Menzel, Lubbock, TX (US)

(73) Assignee: Texas Tech University, Lubbock, TX (US)

(*) Notice: Subject to any disclaimer, the term of this patent is extended or adjusted under 35 U.S.C. 154(b) by 0 days.

(21) Appl. No.: 09/487,702

(22) Filed: Jan. 19, 2000

Related U.S. Application Data (60) Provisional application No. 60/118,805, filed on Feb. 4, 1999, provisional application No. 60/138,294, filed on Jun. 9, 1999, provisional application No. 60/150,527, filed on Aug. 25, 1999, and provisional application No. 60/170,484, filed on Dec. 13, 1999.

(51) Int. Cl.$^7$ .................................................. G01N 21/64
(52) U.S. Cl. ........................................... 436/172; 436/174
(58) Field of Search ............................. 250/458.1, 259.1; 436/164, 172, 174; 422/82.08

(56) References Cited

U.S. PATENT DOCUMENTS

| | | | |
|---|---|---|---|
| 4,983,846 | * | 1/1991 | Rios et al. ......................... 250/458.1 |
| 5,099,131 | * | 3/1992 | Brownrigg et al. ............... 250/458.1 |
| 5,485,530 | * | 1/1996 | Lakowicz et al. ................... 382/191 |
| 5,623,553 | * | 4/1997 | Sekiya ................................. 382/127 |
| 5,714,166 | * | 2/1998 | Tomalia et al. ...................... 424/486 |
| 5,990,479 | * | 11/1999 | Weiss et al. ......................... 250/307 |
| 6,127,189 | * | 10/2000 | Joullie et al. ......................... 436/111 |
| 6,204,068 | * | 3/2001 | Soini .................................... 436/518 |
| 6,207,392 | * | 3/2001 | Weiss et al. ........................... 435/7.1 |

OTHER PUBLICATIONS

Allred, C. E., et al., Forensic Sci. Int. 85, 83–94 (1997).
Allred, C. E., et al., J. Forensic Ident. 47, 542–556 (1997).
Lock, E. R. A., et al., J. Forensic Sci. 40, 654–658 (1995).
Menzel, E. R., et al., J. Forensic Sci. 28, 307–317 (1983).
Ogawa, S., et al., J. Phys. Chem. 99, 11182–11189 (1995).
Sooklal, K., et al., Adv. Mater. 10, 1083–1087 (1998).
Balogh, L., et al., J. Am. Chem. Soc. 120, 7355–7356 (1998).
Bruchez, Jr., M., et al., Science 281, 2013–2016 (9/98).
Menzel, E. R., Anal. Chem. 61, 557A–561A (1989).
Menzel, E. R., Forensic Sci. 35, 35–45 (1990).
Steigerwald, M. L., et al., J. Am. Chem. Soc. 110, 3046–3050 (1988).
Tomalia, D. A., et al., Polymer J. 17, 117–132 (1985).
Center For Forensic Studies of Texas Tech University Web Site (www.phy.ttu.edu/cfs)—updated Aug. 10, 1999.
Chan, W. C. W., Science 281, 2016–2018 (1998).
Menzel, E. R., et al., Proc SPIE 2941, 96–101 (1997).
Menzel, E. R., Fingerprint Detection with Lasers, $2^{nd}$ ed., revised and expanded, Marcel Dekker, New York 1999, Appendix 4.
Wilkinson, D. A., Proc. Int. Symp. on Fingerprint Detection and Identification, Ne'urim, Israel, pp 79–83 (1995.
Wilkinson, D. A., et al., Forensic Sci Int. 60, 67–79 (1993).
Hines, M. A., et al., J. Phys. Chem. 100, 468–471 (1996).
Murdock, R. H., et al., J. Forensic Sci. 38, 521–529 (1993).
Zhao, M., et al., J. Am. Chem. Soc. 120, 4877–4878 (1998).

* cited by examiner

*Primary Examiner*—Jeffrey Snay (57) ABSTRACT

Photoluminescence lifetimes are obtained by attaching photoluminescent semiconductor nanocrystals or lanthanide complex incorporated in dendrimer to fingerprint residue which are compatible with time-resolved imaging techniques for latent fingerprint detection.

9 Claims, 6 Drawing Sheets

FINGERPRINT DEVELOPMENT METHODS

CROSS-REFERENCE TO RELATED APPLICATIONS

This application claims the benefit of U.S. Provisional Applications Nos. 60/118,805, filed Feb. 4, 1999; 60/138,294, filed Jun. 9, 1999; 60/150,527, filed Aug. 25, 1999; and 60/170,484, filed Dec. 13, 1999.

TECHNICAL FIELD

This invention is directed at methods of photoluminescence detection of latent fingerprints.

BACKGROUND OF THE INVENTION

The photoluminescence detection of latent fingerprints has in the last twenty years become a very successful methodology. However, there are still all too many items that defy processing because of intense background fluorescence from the article itself Time-resolved approaches involving gated (time-domain) and phase-resolved (frequency-domain) imaging are being explored to permit background suppression. From the instrumentation perspective, gated imaging is mature. Although photoluminescence lifetimes of microsecond order and even shorter are amenable in principle to gated fingerprint imaging, practicality considerations generally call for lifetimes of millisecond order. The pertinent fingerprint treatments, largely involving lanthanide-based strategies that mostly utilize europium complexes, leave much to be desired for detection on porous surfaces of fingerprints that are not fresh, however. Moreover, while phase-resolved imaging systems have been operational for some time in cell microscopy, for instance, and instruments for fingerprint work are under development, these systems are suitable for photoluminescence lifetimes of nanosecond order, but the needed companion fingerprint treatment strategy has yet to be developed.

SUMMARY OF THE INVENTION

The methods herein allow time-resolved imaging techniques for latent fingerprint development.

One embodiment herein is directed at a method for photoluminescence detection of latent fingerprints, comprising the steps of attaching photoluminescent nanocrystals to fingerprint residue, exciting the nanocrystals to luminescence and detecting fingerprint luminescence. In this embodiment, the nanocrystals can be applied per se or can have their surfaces covered with agent for attachment to fingerprint residue or can be present in nanocomposites with dendrimer and the results can be enhanced by utilizing diimide treatment.

Another embodiment herein is directed at a method for photoluminescence detection of latent fingerprints, comprising the steps of attaching to fingerprint residue lanthanide complex incorporated into dendrimer, exciting the lanthanide complex to huminescence and detecting fingerprint luminescence.

While photoluminescent semiconductor nanocrystals have not heretofore been applied to fingerprint detection, they are known in the biochemistry arena. See Bruchez, Jr., M., et al., Science 281, 2013–2016 (1998); Chan, W. C. W., et al, Science 281, 2016–2018 (1998). They have the same definition here which is particles of semiconductor material with sizes of nanometer order that may be encapsulated and functionalized with organic ligands.

The term "fingerprint residue" is used herein to mean the material left behind on an article when it is touched by a finger.

The term "latent fingerprint" is used to mean a fingerprint left on an article that cannot be discerned on ordinary visual inspection in room light.

DETAILED DESCRIPTION

We turn now to the embodiment herein directed at a method for photoluminescence detection of latent fingerprints, comprising the steps of attaching photoluminescent semiconductor nanocrystals to fingerprint residue, exciting the nanocrystals to luminescence and detecting fingerprint luminescence.

As indicated above, the photoluminescent semiconductor nanocrystals are already known for use in the biochemistry arena and those suitable for use in the biochemistry arena are suitable for use here. They are also referred to as nanocrystalites, quantum dots, nanoparticles, nanoclusters, and sometimes when used in combination with other agents as nanocomposites. They can be formed, for example from CdS, CdSe, CdTe, InP and InAs. They are subcolloidal in size, i.e., smaller than the colloidal silver particles of physical developers, and have diameters on the order of 10 nm, for example, of about 2 to about 5 nm, which is easily small enough for attachment to fingerprint material in the manner of physical developer or, for that matter, the somewhat related approaches involving small particle reagent or even dye staining. They may be soluble in both polar and nonpolar solvents. They can be tailored size-wise to be excitable with light ranging in wavelength from UV to red, luminesce with high quantity yield and lifetimes of about 10 to 100 nanoseconds and can be encapsulated to provide additional benefits as described below.

The attaching referred to can be physical and/or chemical and direct and/or indirect, i.e., mediated by one or more other agents.

For physical attachment, the fingerprint can be fumed with cyanoacrylate ester. This is a known procedure and is described, for example, in Menzel, E. R., et al., J. Forensic Sci. 28, 307–317 (1983). This procedure involves the polymerization at the site of the fingerprint of cyanoacrylate ester molecules. The polymer stabilizes the fingerprint such that subsequent application of solvent such as methanol does not wash away fingerprint detail. The polymer itself also serves as a binding site.

For chemical attachment, the nanocrystal is encapsulated with or incorporated with an agent that reacts with the fingerprint, e.g., lipid (fatty acid) and/or amino components of fingerprint residue.

Encapsulating agents can serve a variety of functions. These functions include passivation to optimize the luminescence efficiency and band width, serving to bind to target molecules of the fingerprint thereby labeling the fingerprint with the photoluminescent semiconductor nanocrystals, serving as the site for chemical attachment of conjugating ligands that also bind to target molecules to thereby fluorescently label them with the photoluminescent semiconductor nanocrystals, serving to solubilize the crystals (e.g., surfactant function), and preventing aggregation of the nanocrystals.

For example, zinc sulfide capping of nanocrystals and silica capping of nanocrystals provide the function of providing sites for chemical attachment of conjugating ligands that also bind to target molecules. ZnS-capped nanocrystals, e.g., ZnS-capped CdSe (cadmium selenide) nanocrystals, can be covalently coupled to amino acids of fingerprint material via conjugating ligands such as mercaptoacetic acid or similar molecules with carboxylate functional groups that are bound to the nanocrystal. Similarly, the capped nanocrystals can be covalently attached to carboxylic acid groups of fingerprint material via conjugating ligands that have amino functionality, such as small proteins that are bound to the nanocrystal. Morever, silica capped nanocrystals, e.g., CdSe nanocrystals, can be covalently attached to amino groups or fatty acids of fingerprint material via conjugating ligands.

ZnS-capped CdSe nanocrystals can be prepared, for example, as described in Hines, M. A. et al., J. Phys. Chem 100, 468–471 (1996).

Moreover, dioctyl sulfosuccinate (sodium salt) encapsulation of nanocrylstals provides a surfactant function to aid in distribution and dissolution and prevent aggregation. For example, dioctyl sulfosuccinate (sodium salt) encapsulated photoluminescent CdS nanocrystals can be prepared as described in Ogawa, S., et al., J. Phys. Chem. 99, 11182–11189 (1995) or Steigerwald, M. L., et al., J. Am. Chem. Soc. 110, 3046–3050 (1988). The dioctyl sulfosuccinate capped CdS nanocrystals can be applied to fingerprint residue that is fumed with cyanoacrylate ester by immersion of article containing the fingerprint in hexane or heptane solution of the encapsulated CdS nanocrystal or to unfumed fingerprint residue on black electrical tape; gentle rinsing with solvent may be necessary to remove excess nanocrystal deposition.

For chemical attachment, the photoluminescent semiconductor nanocomposites can be utilized in the form of aggregates of photoluminescent semiconductor nanocrystals with dendrimer, that is the photoluminescent semiconductor nanocrystals are present in nanocomposites together with dendrimer for attachment to fingerprint residue or to cyanoacrylate ester polymer coating on fingerprint residue. Nanocrystals may also be deposited within voids of the dendrimers or even be prepared in situ within these voids. Nanocomposites of photoluminescent semiconductor nanocrystals and dendrimers are already known but as suggested above, they have not heretofore being used for fingerprint detection; see Zhao, M., et al., J. Am. Chem. Soc. 120, 4877–4878 (1998) and Balogh, L., et al., J. Am. Chem. Soc. 120, 7355–7356 (1998).

In one case, the dendrimer is functionalized with terminal amino groups. In this case, the dendrimer functions to label (bind to) the fingerprint and also serves as host for attaching the photoluminescent tag. Suitable dendrimers of this type (with terminal amino groups) include Generation 0 to 4 Starburst® (PAMAM) dendrimers which are commercially available from Aldrich; these have between 4 and 64 terminal amino groups respectively and as purchased come in methanol solution. Dendrimers of this type are described in Tomalia, D. A., et al., Polymer J. 17, 117–132 (1985). The amino groups of the dendrimer bind the photoluminescent semiconductor nanocrystal to, for instance, fatty acid groups of fingerprint residue by reacting with the fatty acid groups to form amide bonds. The Generation 4 Starburst® dendrimer was found to give best results of the amino terminated dendrimers tried.

The photoluminescent semiconductor nanocrystals are preferably formed in situ in the forming of the nanocrystal/dendrimer nanocomposite. Preparation of methanol solutions of CdS nanocrystal/dendrimer nanocomposites is readily carried out by diluting the purchased dendrimer solution with methanol, and adding to it, repetitively, in small quantities, equal volumes of equimolar methanol solutions of cadmium nitrate and sodium sulfide. It does not matter whether the cadmium nitrate is added to the dendrimer solution, followed by the sodium sulfide, whether the sequence is reversed, or whether both are added simultaneously. Repetitive additions (at room temperature) of cadmium nitrate and sodium sulfide can involve, for example, 5 or 10 aliquots of each reagent. Solutions of the nanocomposite in 10% methanol/90% water can be formed similarly, by diluting the dendrimer methanol solution that was purchased with water to give 1:9 methanol:water and adding the cadmium nitrate and sodium sulfide dissolved in 1:9 methanol:water mixture. While combination of cadmium nitrate and sodium sulfide solutions normally results in cadmium sulfide forming as a precipitate, in the presence of the dendrimer, a nanocomposite forms involving nanocomposites of cadmium sulfide molecules bound to dendrimer molecules or to aggregates of dendrimer molecules. Formation of nanocomposites of this type is described in Sooklal, K., et al., Adv. Mater. 10, 1083–1087 (1998). For Generation 4 Starburst® dendrimers in methanol, the observed luminescence was generally blue-green regardless of CdS concentration in the nanocomposite, but the luminescence intensity increases with CdS concentration. Optimum CdS/Generation 4 dendrimer concentrations in methanol were found to be $8 \times 10^{-4} M/2 \times 10^{-5} M$; this combination forms solutions that are stable at room temperature for at least several days. For 1:9 methanol:water solutions, the optimum CdS/Generation 4 dendrimer concentration was found to be $2 \times 10^{-4} M/8 \times 10^{-5} M$.

Enhancement of the results obtained with nanocomposite of photoluminescent agent and dendrimer functionalized with terminal amino groups is obtained for unfumed fingerprints by treating the fingerprint residue with diimide, preferably water-soluble diimide, prior to immersion of fingerprint residue for application of the nanocomposite. The diimide is considered to react with fatty acid in fingerprint residue according to the following reaction scheme where RCOOH represents the fingerprint carboxylic acid, R'—N=C=N—R" represents the diimide, R'"—NH$_2$ represents the dendrimer and RCONHR'" represents the formed amide, namely the tagged fingerprint:

Diimide mediation of attachment of dendrimer with amino terminal groups to carboxyl groups is known and diimides useful for this are known. A suitable water soluble diimide for use herein is 1-(3-dimethylaminopropyl)-3-ethylcarbodiimide hydrochloride. A solution of 2.5% by weight diimide in water was found to be useful. Diimide pretreatment of fingerprint residue is readily carried out by immersing the fingerprint in the diimide solution. Immersion time spans from about 5 to 24 hours were found to provide substantially enhanced CdS/amino terminated development of fingerprint detail, with the enhancement increase leveling off by 24 hours.

Diimide enhancement can also be carried out by a sequence of steps comprising immersing the fingerprint in the diimide solution, then rinsing, then immersing in dendrimer solution (without photoluminescent semiconductor nanocrystal), then rinsing, then immersing in solution where photoluminescent semiconductor nanocrystals are formed in situ, then rinsing.

In another case, the dendrimer is functionalized with carboxylate groups. For this case, diimide treatment of the dendrimer is necessary. In this alternative, the sequence is reacting diimide with dendrimer functionalized with carboxylate groups, for example, by adding the diimide in stoichiometric amount to solution of dendrimer and heating, for example, at 60° C. overnight, then forming luminescent semiconductor nanocrystal in situ in the solution, then fingerprint immersion in the solution. The use of stoichiometric amount of diimide is intended to minimize formation of ester in the fingerprint residue itself upon subsequent sample immersion, which would tie up amino acid in fingerprint residue that otherwise could react with dendrimer. Heating, e.g., to 50 to 70° C. and reaction times of 8–20 hours, provide fingerprint development that is suitably intense. The reaction scheme given above with respect to diimide applies here as well, except that RCOOH represents the carboxylate function on dendrimer and R'''—$NH_2$ represents amino group on fingerprint material. Suitable water-soluble dendrimer is Generation 3.5 Starburst® dendrimer from Aldrich where each molecule contains 64 carboxylate (sodium salt) terminal groups. The diimides for this case are preferably water soluble and are the same as those described above with 1-(3-dimethylaminopropyl)-3-ethylcarbodiimide hydrochloride being used in the working example herein.

In an embodiment herein the photoconductor semiconductor nanocrystals are CdSe nanocrystals and these are encapsulated with ZnS as described above and in one case functionalized with amino groups by, e.g., using small proteins as described above, and in another case functionalized with carboxylate groups via conjugating ligands such as mercaptoacetic acid as described above. In the case of functionalization with carboxylate groups, diimide treatment (the same as in the case of dendrimer functionalized with carboxylate groups described above) is necessary.

As indicated above, the photoluminescent semiconductor nanocrystals are normally formed in solution, and these solutions can include dendrimer with terminal amino groups or dendrimer with terminal carboxylate groups. The appropriate fingerprint residue component or dendrimer functional group or nanocrystal functional group may be reacted with diimide. The fingerprints are immersed in the solution. Where there is no chemical reaction with fingerprint residue, immersion times are uncritical and immersion times ranging from a few seconds to a few minutes are normally used. Where chemical reaction with fingerprint residue or with cyanoacrylate ester polymer coating thereon is desired, immersion time is time suitable for reaction, e.g., about 5 to 24 hours. Spraying of fingerprint-containing articles may be applied as well.

On removal from immersion, the fingerprints are allowed to dry so as to be dry to the touch. This condition normally is obtained in a few minutes.

Then excitation of the photoluminescent semiconductor nanocrystals is carried out, e.g., using an Ar-laser operating in near UV (about 50 mW) or a filtered lamp. Additional suitable excitation conditions using, e.g., an Ar-laser operating in the blue-green or, e.g., a dye laser operating in the green to red, pertain depending on the particular nanocrystal used. The excitation causes fingerprint readings where nanocrystals attach to fluoresce. The luminescence obtained is in high quantum yield with lifetimes ranging from about 10 to about 1,000 nanocrystals. This provides fingerprint luminescence lifetime significantly different from that of the background thereby enabling phase-resolved and even gated imaging.

Upon excitation, fingerprint luminescence is detected, for example, by photographing or detection by gated or phase-resolved imaging because of the suitable lifetimes of luminescence obtained. Pertinent phase-resolved imaging approaches are discussed, for example, in Menzel, E. R., Fingerprint Detection with Lasers, $2^{nd}$ ed., revised and expanded, Marcel Dekker, New York 1999, which is incorporated herein by reference.

We turn now to the embodiment herein directed to method for photoluminescence detection of latent fingerprints comprising the steps of attaching to fingerprint residue lanthanide complex incorporated into dendrimer, exciting the lanthanide complex and detecting fingerprint luminescence. Except for the inclusion of dendrimer, the method is old and the method is described, for example, in Menzel, E. R., Anal Chem. 61; 557A–561A (1989); Menzel, E. R., et al., J. Forensic Sci 35, 35–45 (1990); Wilkinson, D. A., Proc. Int Symp. on Fingerprint Detection and Identification, Néurim, Israel, pp 79–83 (1995); Wilkinson, D. A., et al., Forensic Sci. Int. 60, 67–79 (1993); Lock, E. R. A., et al., J. Forensic Sci. 40, 654–658 (1995); Allred, C. E., et al., Forensic Sci. Int. 85, 83–94 (1997); Allred, C. E., et al., J. Forensic Sci. 47, 542–556 (1997); Menzel, E. R., et al., Proc. SPIE 2941:96–101 (1997); and Menzel, E. R., Fingerprint Detection with Lasers, $2^{nd}$ ed., revised and expanded, Marcel Dekker, New York (1999); the whole of each of which is incorporated herein by reference. In these, the lanthanide complexes are usually europium complexes but terbium complexes are also of interest. Chelation is with a ligand that absorbs well and that transfers its excitation energy to the lanthanide ion, basically the Forster energy transfer process. The current most effective application of lanthanides to fingerprint detection involves the staining approach using europium with thenoyltrifluoroacetone and/or ortho-phenanthroline as sensitizing ligands. Preparation of lanthanide complexes can involve mixing $EuCl_3.6H_2O$ with an excess of ligand or a stoichiometric proportion (the full coordination of the $Eu^{3+}$ ion being ninefold). This known method detects poorly on porous surfaces fingerprints that are not fresh. The method of the instant invention involving lanthanide complexes solves this problem. As indicated above, the method herein involving lanthanide complexes differs from what has been done before in that the highly luminescent lanthanide complexes are incorporated into a dendrimer. The dendrimers involved contain the same terminal functional groups as discussed above and are the same as those discussed above having this functionality. The incorporation of the lanthanide complexes into the dendrimers is carried out by adding lanthanide complex solution to dendrimer solution. The immersion of the fingerprints and excitation is the same as used in conjunction with lanthanide complex fingerprint detecting techniques before. The excitation provides luminescences of milisecond-order lifetimes suitable for gated imaging to suppress background fluorescence. The gated imaging techniques are available for use and are known to those skilled in the art. A suitable gated imaging technique is described in Murdock, R. H., et al., J. Forensic Science 38, 521–529 (1993).

Elements of the inventions herein are described in related U.S. Provisional Patent Application Nos. 60/118,805, 60/138,294, 60/150,527, and 60/170,484, the whole of all of which is incorporated herein by reference.

The methods herein are illustrated by the following examples wherein the sample fingerprints are latent fingerprints.

EXAMPLE I

Use of CdS Nanocrystals Capped with Dioctyl Sulfosuccinnate

CdS nanocrystals, prepared in inverse micelles were capped with dioctyl/sulfosuccinate (sodium salt). These were used for fingerprint detection, dissolved in heptane and hexane.

Figure 1:
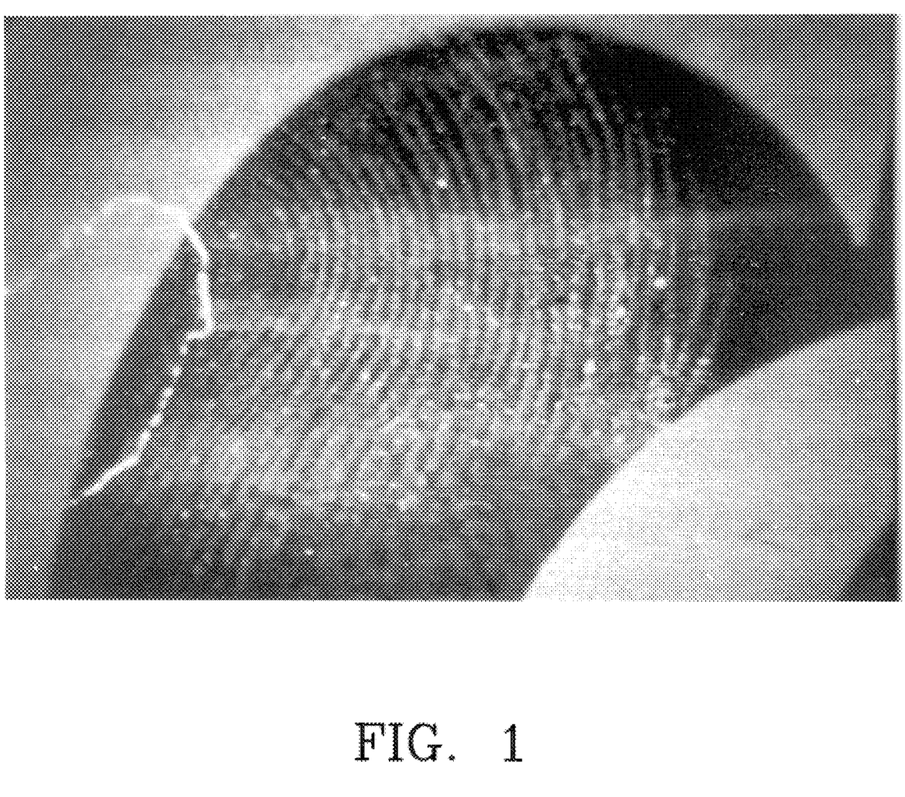
FIG. 1 depicts a fingerprint detected on a soft drink can fumed with cyanoacrylate ester and stained with CdS nanocrystals and shows a result of Example I.

Sample fingerprints placed on aluminum foil and a soft drink can were fumed with cyanoacrylate ester and then immersed for times ranging from a few seconds to a few minutes in the nanocrystal solutions. The immersion times were not critical. The samples were then left to dry. Examination under an Ar-laser operating in the near-UV revealed amply intense luminescence, easily visible. However, there was a generally heavy coverage of the immersed region, with no fingerprint ridge detail discernible. The samples were thus subjected to a gentle rinsing with hexane, to remove excess nanocrystal deposition, leaving behind fingerprint detail. A fingerprint detected on the soft drink can fumed with cyanoacrylate ester and stained with CdS nanocrystals is shown in FIG. 1.

Unfumed fingerprints on metal, glass and plastics, which normally are fumed, could not be developed. The reason is that hexane and heptane are rather good solvents for non-polar substances generally, and fingerprint lipids in particular. Thus, they very immersion of the article in the nanocrystal solution tended to obliterate ridge detail. In this respect, hexane is a more aggressive solvent than heptane because of its substantially lower viscosity.

Fingerprints on black plastic electrical tape immersed in the CdS nanocrystal solution in heptane and rinsed with heptane developed fairly readily without cyanoacrylate ester pretreatment.

EXAMPLE II

Use of CdS/Generation 4 Starburst® Dendrimer Nanocomposite

CdS Generation 4 Starburst® dendrimer nanocomposites in methanol and 1:9 methanol water solutions were formed as described above (CdS/Generation 4 dendrimer concentration of $8\times10^{-4}M/2\times10^{-5}M$ in methanol and $2\times10^{-4}/8\times10^{-5}M$ in 1:9 methanol:water solution.

Figure 2:
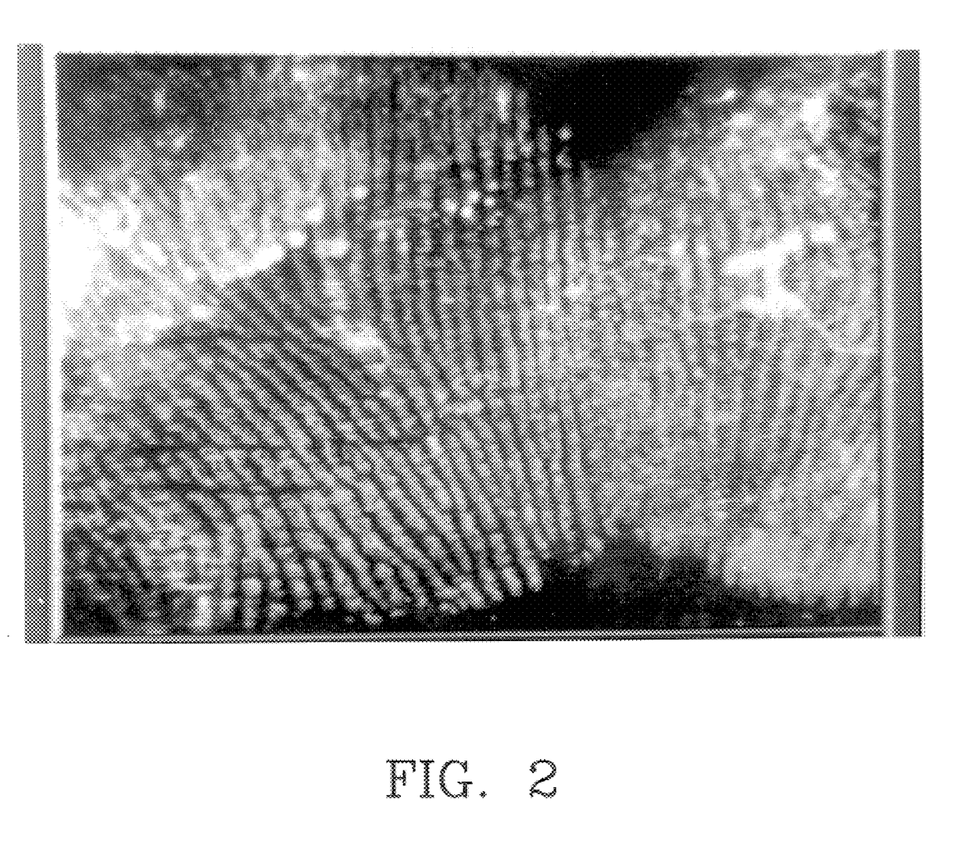
FIG. 2 depicts a fingerprint on aluminum foil fumed with cyanoacrylate ester and developed with methanol solution of CdS/Generation 4 dendrimer and shows a result of Example II.

Aluminum foil and polyethylene samples with fingerprints thereon (fresh to one-day-old) were placed in CdS/dendrimer solution and let dry completely. The immersion was typically overnight. Methanol solution dipped fumed prints developed readily. A fingerprint detected on aluminum foil fumed with cyanoacrylate ester and developed with methanol solution of CdS/Generation 4 dendrimer is shown in FIG. 2. Methanol solution dipping was not successful on unfumed fingerprints because the methanol solvent tended to wash away the fingerprints. Methanol:water solution dipped fumed and unfumed prints developed readily. Prints under near-ultraviolet excitation (about 50 mW) from an Ar-laser were photographed with a digital camera (Kodak DC 120).

Adherence of the nanocomposite everywhere precluded detection of unfumed fingerprints on paper.

Solutions of Generation 0 Starburst® dendrimer and of Generation 1 Starburst® dendrimer in place of the Generation 4 dendrimer with methanol as the only solvent in the testing described above allowed detection but the luminescence intensity obtained from the fingerprints was not as good as when Generation 4 dendrimer was used. Solutions of Generation 0 and Generation 1 dendrimer, together with cadmium nitrate and sodium sulfide, could not be made up in 1:9 (by volume) methanol:water; precipitation occurred in all cases.

EXAMPLE III

Use of CdS/Generation 4 Starburst® Dendrimer Nanocomposite in Conjunction with Diimide Treatment In this experiment, fingerprints were pre-treated with diimide.

The initial fingerprint treatment by diimide utilized 1,3-dicyclohexylcarbodiimide. As obtained commercially, this non-polar compound comes in 1M dichloromethane solution. For reasons of economy, this solution was diluted with dichloromethane. A 2.5% diimide by weight working solution was made up. Both cyanoacrylate fumed and unfumed fingerprints (on aluminum foil, polyethylene, and paper in the unfumed case) were immersed in the diimide solution (at room temperature) for varying amounts of time. Since the cyanoacrylate polymer formed on fingerprint fuming already contains ester moieties, no effect should result from exposure to diimide. The immersion of fumed prints thus was intended to serve as a control experiment. Indeed, comparison of fumed fingerprints that were immersed in the diimide and fingerprints that were immersed for equal times in neat dichloromethane showed no differences in development after subsequent treatment with CdS/Generation 4 dendrimer and luminescence examination. Unfumed fingerprints could be exposed to the diimide solution or dichloromethane solvent only for short times (on the order of minutes) because the fingerprints tended to be dissolved. With such short immersion times, no appreciable difference in the subsequent CdS/dendrimer development of fingerprints was found. Because the CdS/dendrimer nanocomposite tends to adhere everywhere on polyethylene, not just to fingerprints, the results with this material were difficult to visualize. A similar background problem was found with paper as well. Thus, the work described below focused on fingerprints (fresh to 2-weeks-old) on aluminum foil. Because of dissolution of fingerprint constituents in the aggressive dichloromethane, the use of a diimide soluble in water was examined, namely 1-(3-dimethylaminopropyl)-3-ethylcarbodiimide hydrochloride. Initially, the solvent system selected was the 1:9 methanol:water mixture of Example II of CdS/dendrimer development of unfumed fingerprints. Prolonged immersion in this diimide solution resulted in chemical attack on the aluminum foil itself, however. Thus, the methanol was deleted and the diimide fingerprint pre-treatment used a standard solution of 2.5% diimide (by weight) in water. Fingerprints immersed in water alone for the same time served as controls. CdS/Generation 4 dendrimer fingerprint processing utilized $2\times10^{-4}$ M/$8\times10^{-5}$ M nanocomposite formulation and 1:9 methanol:water solvent system, as described in Example II.

Figure 3:
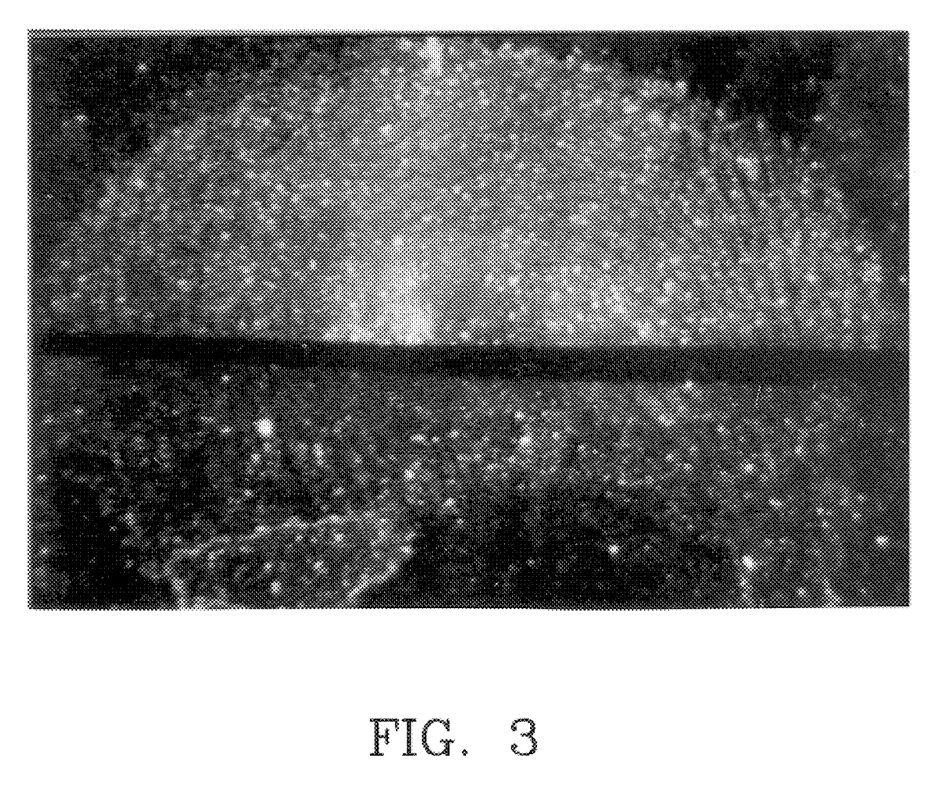
FIG. 3 depicts fingerprint development with CdS/Generation 4 dendrimer with (top half) and without (bottom half) carbodiimide and shows results of Example III.

Diimide pre-treatment of fingerprint halves for times ranging from seconds to roughly one hour produced no enhancement over the corresponding water-immersed control-halves. For time spans from about 5 to 24 hours, substantially enhanced CdS/dendrimer development of fingerprint detail was found, however, with the enhancement increase leveling off by 24 hours. These observations indicate predominant chemical attachment. Since chemical reaction rates increase with temperature increase, diimide pre-treatment at 60° C. was carried out to compare with the pre-treatment above at room temperature. At the 60° C. temperature, however, chemical attack on the aluminum foil substrate itself occurred for heating times longer than about one hour. With shorter heating times, no enhancement increase with heating was observed. Moreover, CdS/dendrimer solution caused increase in fingerprint development with increase in temperature without diimide pre-treatment as indicated by comparison of two halves of a fingerprint developed for 5 hours at 60° C. and at room temperature; this indicates chemical binding of nanocomposite to fingerprint residue even in the absence of diimide treatment. FIG. 3 shows fingerprint development with CdS/Generation 4 dendrimer with (top half) and without (bottom half) diimide treatment.

EXAMPLE IV

Use of CdS/Diimide Treated Generation 3.5 Dendrimer Nanocomposite

CdS/dendrimer nanocomposites were used as in Example II except that the dendrimer was Generation 3.5 Starburst® dendrimer containing 64 terminal groups which have carboxylate (sodium salt) functionality.

Figure 4:
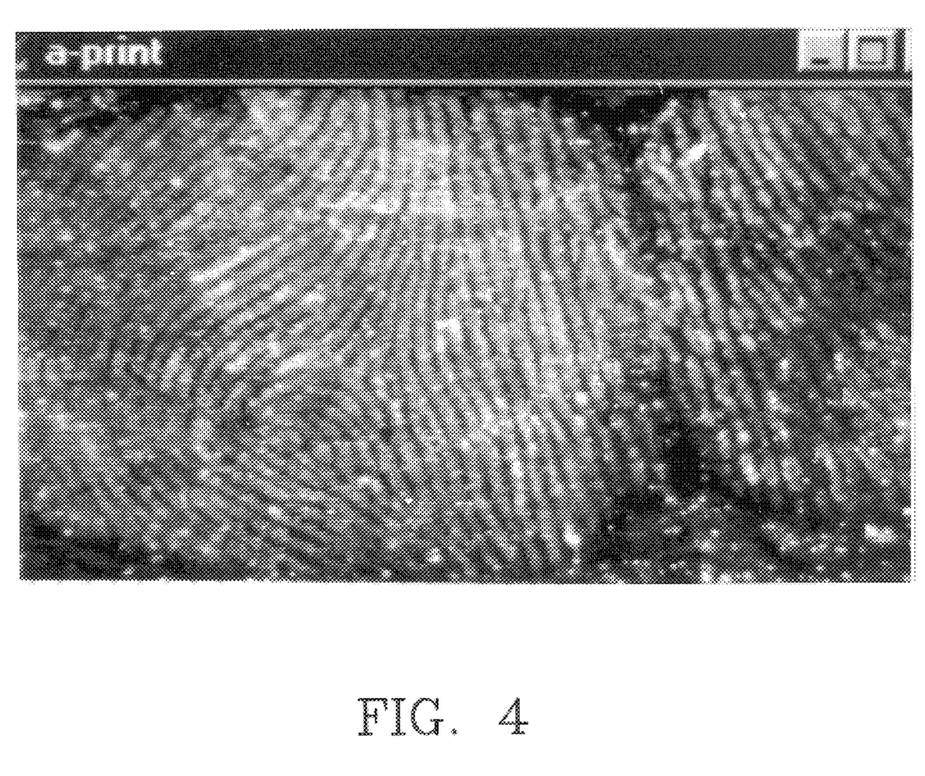
FIG. 4 depicts a CdS/Generation 3.5 dendrimer developed fingerprint in the presence of carbodiimide and shows a result of Example IV.

Solutions were made up in methanol as well as in 1:9 (by volume) methanol:water solvent with $2\times10^{-4}$ M/$8\times10^{-5}$ M CdS/dendrimer concentration. As with Generation 4 dendrimer, the methanol solution formation was ineffective with unfumed fingerprint samples. With fumed fingerprints, the results were roughly comparable to Generation 4 dendrimer in Example II, with no advantage presented by Generation 3.5 dendrimer. The 1:9 methanol:water formulation of CdS/Generation 3.5 dendrimer produced no fingerprint development at all for unfumed fingerprints on aluminum foil (or polyethylene), in contrast to what is obtained with the Generation 4 dendrimer counterpart. This is not surprising because different ingredients of the fingerprint residue are targeted. Lipid-rich fingerprint residue pertains to our study (e.g., from fingers rubbed on the forehead). Thus, the protein or amino acid of interest (to CdS/Generation 3.5 dendrimer) might be expected to be buried among or beneath the lipids present. The situation would be aggravated by the fact that the polar reagent solvent system is inherently incompatible with the non-polar lipids. This incompatibility is reminiscent of what is encountered in lipid fingerprint development with lanthanide chelates. There, the solution to the difficulty involved addition to the solvent system of a small amount of acetone for the purpose of lipid solubilization. The same approach was employed here, with acetone concentrations up to 20% by volume added to the 1:9 methanol:water solution. The acetone additions produced only sporadic fingerprint development with Generation 3.5 dendrimer upon sample (fingerprint on aluminum foil) immersions for as many as four days. In contrast, crisp luminescent detail was consistently found with Generation 4 dendrimer after such immersions. This suggested that the solubilization issue was not the cause for failure but that instead the poor suitability of the dendrimer's carboxylate functionality for attack on the amino acids of fingerprint residue was the cause. Thus, the treatment of Generation 3.5 dendrimer with diimide prior to fingerprint treatment was examined. The successful sequence (in 1:9 methanol:water) was: Generation 3.5 dendrimer+stoichiometric amount of 1-(3-dimethylaminopropyl)-3-ethylcarbodiimide hydrochloride (keeping in mind that 64 functional groups are present in each dendrimer molecule)+heating at 60° C. overnight+CdS incorporation+fingerprint immersion. The stoichiometric addition of diimide (about $2.4\times10^{-4}$M dendrimer: $1.5\times10^{-2}$M diimide) was intended to minimize formation of ester in the fingerprint residue itself upon subsequent sample immersion, which would tie up amino acid that otherwise could react with dendrimer. The heating step was essential. Without it fingerprint development was very faint only. The 1-(3-dimethylaminopropyl)-3-ethylcarbodiimide hydrochloride attacks aluminum foil to give it a tarnished appearance much like tarnished silver. In absence of the heating step, the subsequently immersed aluminum foil fingerprint samples acquire this tarnishing, and there thus is a concomitant counterproductive reaction of the diimide with carboxylic acid of the fingerprint residue. In presence of the heating step, no aluminum foil tarnishing is seen, indicating that the diimide indeed reacts with the dendrimer, as is desired. FIG. 4 shows a CdS/Generation 3.5 dendrimer developed fingerprint in the presence of carbodiimide. CdS/dendrimer nanocomposite formation followed by diimide addition was not a successful sequence, perhaps because of excessive aggregation preceding the addition of the diimide. Some indication of this is provided by the substantial red-shift in solution luminescence for dendrimer+CdS+diimide compared to dendrimer+diimide+CdS. The luminescence is orange, in contrast to the yellow-green one for Generation 4 dendrimer and diimide pre-treatment. It is nicely excitable by near-ultraviolet, as well as blue (albeit rather more weakly). Both are obtainable from Ar-lasers, a convenience for the necessarily laser-based time-resolved imaging instrumentation.

EXAMPLE V

Figure 5:
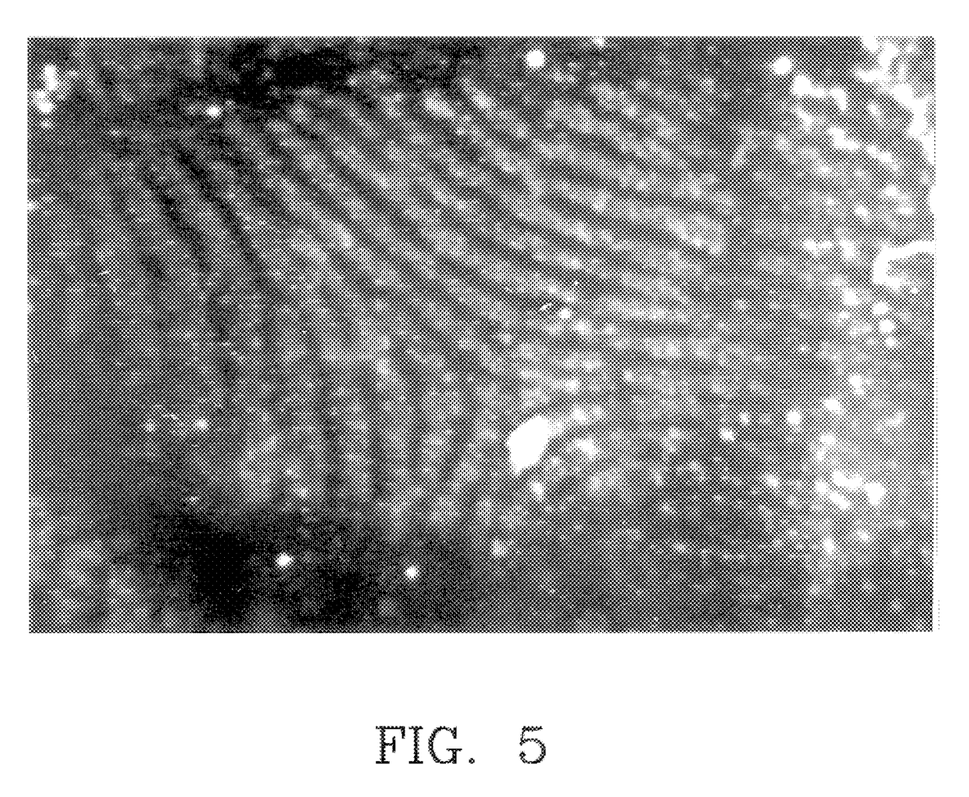
FIG. 5 depicts a fingerprint half detected on aluminum foil developed with carboxylate functionalized ZnS-capped CdSe nanocrystals with carbodiimide mediation and shows a result of Example V.

Use of Carboxylate Functionalized ZnS-Capped CdSe Nanocrystals with Diimide Mediation Aluminum foil samples of latent fingerprints, about one month old, were immersed in water solution containing one micromolar concentration of carboxylate functionalized ZnS-encapsulated CdSe nanocrystals (emitting red luminescence) obtained from Quantum Dot Corporation and eight micromolar concentration of 1-3-dimethylaminopropyl)-3-ethylcarbodiimide hydrochloride. The 1:8 nanocrystal:diimide proportion (one normally would use a larger amount of diimide) was intended to minimize potential flocculation of the nanocrystals. The low concentration of nanocrystal used was simply a matter of limitations in the availability of nanocrystals. Although companies are currently forming for commercialization of nanocrystals, they are still available in experimental quantities only. One would in eventual practice expect to work at much higher concentrations. After immersion for 24 hrs at room temperature, the fingerprint-half shown in FIG. 5 was obtained (under green Ar-laser excitation). The corresponding other fingerprint-half, immersed for the same time in a solution of the same nanocrystal concentration, but without the diimide, showed no development at all. Considerable nanocrystal flocculation did occur over the 24-hour period in the diimide-containing solution. Heating at 60° C. for 5 hrs destroyed solutions (severe flocculation and loss of luminescence). Immersion of fingerprints in solutions at 4° C. for times up to five days produced rather poor development only.

EXAMPLE VI

Use of Lanthanide Chelate with Dendrimer

Figure 6:
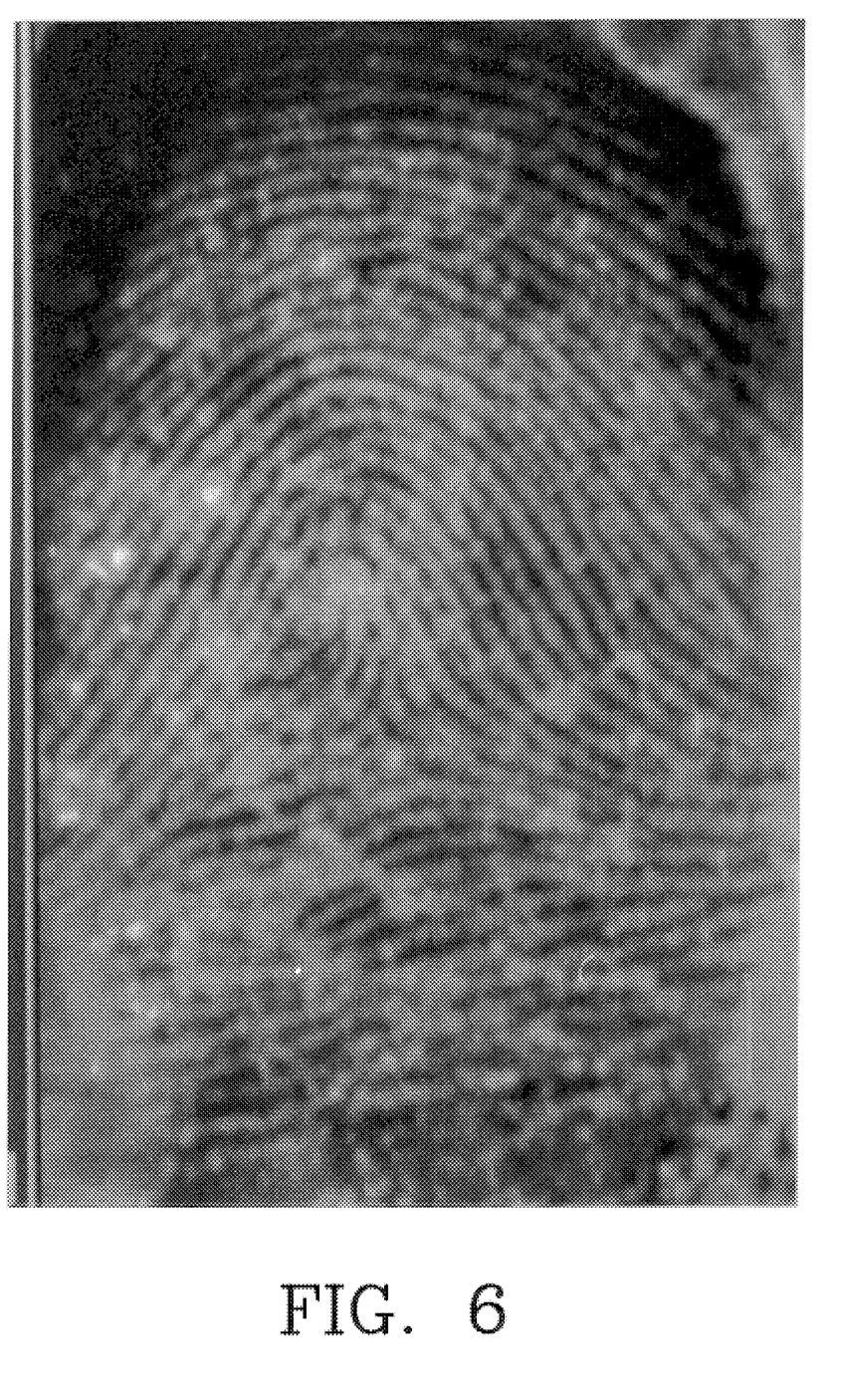
FIG. 6 depicts an Eu-thenoyltrifluoroacetone chelate/Generation 3.5 Starburst (PAMAM) dendrimer developed fingerprint and depicts a result of Example VI.

Into a 1:9 methanol:water solution made up of $2.4 \times 10^{-4}$M Generation 3.5 Starburst® (PAMAM) dendrimer, five times that concentration of $EuCl_3.6H_2O$, and twenty times that first concentration of thenoyltrifluoroacetone, a sample of aluminum foil containing a latent fingerprint was immersed for 24 hours. The excitation was with near-UV light from an Ar-laser, with the characteristic red luminescence of $Eu^{3+}$ obtained. A fingerprint detected is shown in FIG. 6. Into a control solution that had the same concentrations of the europium compound and the thenoyl compound (to form the lanthanide chelate) but no dendrimer, a similar sample was immersed as well for 24 hrs; no fingerprint development comparable to what is seen in FIG. 6 was obtained.

VARIATIONS

Many variations of the above will be obvious to those skilled in the art. Thus, the invention is defined by the claims.

What is claimed is:

1. A method for photoluminescence detection of latent fingerprints, comprising the steps of attaching photoluminescent semiconductor nanocrystals to fingerprint residue, exciting the nanocrystals to luminesce and detecting fingerprint luminescence.

2. The method of claim 1 where the photoluminescent semiconductor nanocrystals have their surfaces covered with agent for attachment of the nanocrystals to fingerprint residue or to cyanoacrylate ester polymer coating on the fingerprint residue.

3. The method of claim 1 where the photoluminescent semiconductor nanocrystals have their surfaces covered with surfactant.

4. The method of claim 1 where the photoluminescent semiconductor nanocrystals are present in nanocomposites together with dendrimer with terminal amino groups for attachment to fingerprint residue or to cyanoacrylate ester polymer coating on fingerprint residue.

5. The method of claim 4 wherein the fingerprint is treated with diimide prior to attachment of the nanocomposites to fingerprint residue.

6. The method of claim 1 wherein the attaching of photoluminescent semiconductor nanocrystals to fingerprint residue comprises the steps of immersing the fingerprint residue in diimide solution, rinsing, then immersing in dendrimer solution, then rinsing, then immersing in solution where photoluminescent semiconductor nanocrystals are formed in situ, then rising.

7. The method of claim 1 wherein the photoluminescent semiconductor nanocrystals are present in nanocomposites together with dendrimer with terminal carboxylate groups treated with diimide for attachment to fingerprint residue.

8. The method of claim 1 where the fingerprints are fumed with cyanoacrylate ester for attachment of photoluminescent semiconductor nanocrystals.

9. A method for photoluminescence detection of latent fingerprints, comprising the steps of attaching to fingerprint residue lanthanide complex incorporated into dendrimer, exciting the lanthanide complex to luminescence and detecting fingerprint luminescence.

* * * * *